United States Patent
Stadtmueller et al.

(10) Patent No.: US 8,404,674 B2
(45) Date of Patent: Mar. 26, 2013

(54) SUBSTITUTED 9H-PURIN-2-YL COMPOUNDS, COMPOSITIONS THEREOF AND USES THEREOF

(75) Inventors: Heinz Stadtmueller, Ingelheim am Rhein (DE); Guido Boehmelt, Ingelheim am Rhein (DE); Harald Engelhardt, Ingelheim am Rhein (DE); Ulrich Hirt, Ingelheim am Rhein (DE); Otmar Schaaf, Ingelheim am Rhein (DE); Irene Waizenegger, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 463 days.

(21) Appl. No.: 12/595,072

(22) PCT Filed: Mar. 4, 2008

(86) PCT No.: PCT/EP2008/052631
§ 371 (c)(1),
(2), (4) Date: Jun. 15, 2010

(87) PCT Pub. No.: WO2008/107444
PCT Pub. Date: Sep. 12, 2008

(65) Prior Publication Data
US 2010/0311721 A1    Dec. 9, 2010

(30) Foreign Application Priority Data
Mar. 7, 2007 (EP) .................................. 07103669

(51) Int. Cl.
*C07D 519/00* (2006.01)
*A61K 31/52* (2006.01)
*A61P 35/00* (2006.01)

(52) U.S. Cl. ............. 514/211.1; 514/234.2; 514/252.16; 514/263.22; 544/118; 544/277; 540/578

(58) Field of Classification Search .................. 540/578; 514/211.1, 234.2, 252.16, 263.22; 544/277, 544/118
See application file for complete search history.

(56) References Cited

U.S. PATENT DOCUMENTS

| 7,476,670 B2 * | 1/2009 | Bordon-Pallier et al. .. 514/234.2 |
| 2007/0249639 A1 * | 10/2007 | Baenteli et al. ............. 514/263.4 |
| 2008/0261973 A1 * | 10/2008 | Capraro et al. ............. 514/234.2 |
| 2010/0204187 A1 * | 8/2010 | Salas Solana et al. ........ 514/157 |

FOREIGN PATENT DOCUMENTS

| WO | 0109134 A1 | 2/2001 |
| WO | 2004073595 A2 | 9/2004 |
| WO | 2005097135 A2 | 10/2005 |
| WO | 2007071393 A2 | 6/2007 |

* cited by examiner

*Primary Examiner* — Mark Berch
(74) *Attorney, Agent, or Firm* — Michael P. Morris; Mary-Ellen M. Devlin

(57) ABSTRACT

The present invention encompasses compounds of general formula (1)

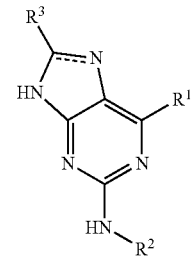

(1)

wherein
$R^1$, $R^2$ and $R^3$ are defined as in claim 1, which are suitable for the treatment of diseases characterized by excessive or abnormal cell proliferation, and their use for preparing a pharmaceutical composition having the above-mentioned properties.

11 Claims, No Drawings

SUBSTITUTED 9H-PURIN-2-YL COMPOUNDS, COMPOSITIONS THEREOF AND USES THEREOF

SEQUENCE LISTING

The instant application contains a Sequence Listing which has been submitted via EFS-Web and is hereby incorporated by reference in its entirety. Said ASCII copy, created on Jun. 11, 2010, is named BIC2269.txt and is 1,071 bytes in size.

The present invention relates to new purines of general formula (1)

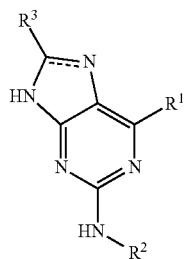

(1)

wherein the groups $R^1$ to $R^3$ have the meanings given in the claims and specification, the isomers thereof, processes for preparing these compounds and their use as medicaments.

BACKGROUND TO THE INVENTION 9H-purine-2,6-diamines are described as topoisomerase II inhibitors in WO 2005/097135.

DETAILED DESCRIPTION OF THE INVENTION

Surprisingly, it has been found that compounds of general formula (1), wherein the groups $R^1$, $R^2$ and $R^3$ have the meanings given hereinafter, act as inhibitors of specific cell cycle or signal transduction kinases. Thus the compounds according to the invention may be used for example for the treatment of diseases connected with the activity of specific cell cycle or signal transduction kinases and characterised by excessive or abnormal cell proliferation.

The present invention relates to compounds of general formula (1)

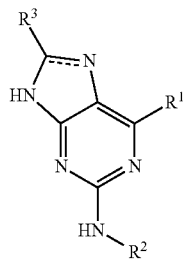

(1)

wherein
the dotted line represents an optional double bond;
$R^1$ denotes 8-12 membered heteroaryl or heterocycloalkyl, optionally substituted by one or more identical or different $R^4$, and;

$R^2$ denotes a group selected from among $C_{6-15}$aryl, 3-8 membered heterocycloalkyl and 5-12 membered heteroaryl, optionally substituted by one or more identical or different $R^4$, and $R^3$ denotes hydrogen or a group selected from among =O, halogen and $C_{1-4}$alkyl; and $R^4$ denotes a group selected from among $R^a$, $R^b$ and $R^a$ substituted by one or more identical or different $R^b$ and/or $R^c$;

each $R^a$ is selected independently of one another from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is a suitable group and each is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)$ $NR^cR^c$, —$NR^cR^c$, —$ONR^cR^c$, —$N(OR^c)R^c$, —$N(R^g)$ $NR^cR^c$, halogen, —$CF_3$, —$CN$, —$NC$, —$OCN$, —$SCN$, —$NO$, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)$ $R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, $N[S(O)_2R^c]_2$, —$N(R^g)$ $S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)$ $[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)_2]$ $NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$ and —$N(R^g)C$ $(NR^g)NR^cR^c$, each $R^c$ independently of one another denotes hydrogen or a group optionally substituted by one or more identical or different $R^d$ and/or $R^e$ selected from among $C_{1-6}$alkyl, $C_{3-10}$cyclo alkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^d$ is a suitable group and each is independently selected from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C$ $(O)NR^eR^e$, —$NR^eR^e$, —$ONR^eR^e$, —$N(R^g)NR^eR^e$, halogen, —$CF_3$, —$CN$, —$NC$, —$OCN$, —$SCN$, —$NO$, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)$ $R^e$, —$C(O)OR^e$, —$C(O)SR^e$, —$C(O)NR^eR^e$, —$C(O)N(R^g)$ $NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)$ $SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)$ $C(O)R^e$, —$N[C(O)R^e]_2$, —$N(OR^g)C(O)R^e$, —$N(R^g)C(NR^g)$ $R^e$, —$N(R^g)N(R^g)C(O)R^e$, —$N[C(O)R^e]NR^eR^e$, —$N(R^g)$ $C(S)R^e$, —$N(R^g)S(O)R^e$, —$N(R^g)S(O)OR^e$, —$N(R^g)$ $S(O)_2R^e$, —$N[S(O)_2R^e]_2$, —$N(R^g)S(O)_2OR^e$, —$N(R^g)$ $S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)$ $NR^gNR^eR^e$, —$N(R^g)N(R^g)C(O)NR^eR^e$, —$N(R^g)C(S)

NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$, each R$^e$ independently of one another denotes hydrogen or a group optionally substituted by one or more identical or different R$^f$ and/or R$^g$ selected from among C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R$^f$ is a suitable group and each is independently selected from among halogen and —CF$_3$; and each R$^g$ independently of one another denotes hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, optionally in the form of the tautomers, the racemates, the enantiomers, the diastereomers and the mixtures thereof, and optionally the pharmacologically acceptable acid addition salts thereof.

In another aspect the invention relates to compounds of general formula (1), wherein R$^1$ is 9-10 membered heteroaryl or heterocycloalkyl, optionally substituted by one or more identical or different R$^4$.

In another aspect the invention relates to compounds of general formula (1), wherein R$^1$ is tetrahydroimidazopyridine or tetrahydroimidazoazepine, optionally substituted by one or more identical or different R$^4$.

In another aspect the invention relates to compounds of general formula (1A), wherein

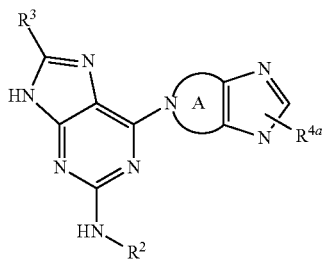

(1A)

A denotes a 5-7 membered aliphatic ring, and

R$^2$ denotes a group selected from among C$_{6-15}$aryl, 3-8 membered heterocycloalkyl and 5-12 membered heteroaryl, optionally substituted by one or more identical or different R$^4$, and R$^3$ denotes hydrogen or a group selected from among halogen and C$_{1-4}$alkyl; and R$^4$ and R$^{4a}$ in each case independently of one another denote a group selected from among R$^a$, R$^b$ and R$^a$ substituted by one or more identical or different R$^b$ and/or R$^c$;

each R$^a$ is selected independently of one another from among C$_{1-6}$alkyl, C$_{3-10}$cycloalkyl, C$_{4-16}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R$^b$ is a suitable group and each is independently selected from among =O, —OR$^c$, C$_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$ and —N(R$^g$)C(NR$^g$)NR$^c$R$^c$, each R$^c$ independently of one another denotes hydrogen or a group optionally substituted by one or more identical or different R$^d$ and/or R$^e$ selected from among C$_{1-6}$alkyl, C$_{3-10}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R$^d$ is a suitable group and each is independently selected from among =O, —OR$^e$, C$_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O) R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O) SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$, each R$^e$ independently of one another denotes hydrogen or a group optionally substituted by one or more identical or different R$^f$ and/or R$^g$ selected from among C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R$^f$ is a suitable group and each is independently selected from among halogen and —CF$_3$; and each R$^g$ independently of one another denotes hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, optionally in the form of the tautomers, the racemates, the enantiomers, the diastereomers and the mixtures thereof, and optionally the pharmacologically acceptable acid addition salts thereof.

In another aspect the invention relates to compounds of general formula (1A), wherein $R^{4a}$ denotes a group selected from among hydrogen, halogen, —$CF_3$, $C_{1-6}$alkyl, wherein the alkyl group is optionally substituted by —$OR^e$.

In another aspect the invention relates to compounds of general formula (1A), wherein A denotes piperidine or azepine, optionally substituted by one or more identical or different $R^{4a}$.

In another aspect the invention relates to compounds of general formula (1A), wherein $R^{4a}$ denotes a group selected from among hydrogen, halogen, —$CF_3$ and $C_{1-6}$alkyl, wherein the alkyl group is optionally substituted by —$R^e$.

In another aspect the invention relates to compounds of general formula (1) or (1A), wherein $R^2$ denotes a group selected from among $C_{6-10}$aryl and 5-12 membered heteroaryl, optionally substituted by one or more identical or different $R^4$.

In another aspect the invention relates to compounds of general formula (1) or (1A), wherein $R^2$ is phenyl, optionally substituted by one or more identical or different $R^4$.

In another aspect the invention relates to compounds of general formula (1), wherein $R^3$ is a group selected from among hydrogen and $C_{1-6}$alkyl.

In another aspect the invention relates to compounds of general formula (1) or (1A), or the pharmaceutically effective salts thereof, for use as pharmaceutical compositions.

In another aspect the invention relates to compounds of general formula (1) or (1A), or the pharmaceutically effective salts thereof, for preparing a pharmaceutical composition with an antiproliferative activity.

In another aspect the invention relates to a pharmaceutical preparation, containing as active substance one or more compounds of general formula (1) or (1A), or the pharmaceutically effective salts thereof, optionally in combination with conventional excipients and/or carriers.

In another aspect the invention relates to the use of compounds of general formula (1) or (1A), for preparing a pharmaceutical composition for the treatment and/or prevention of cancer, infections, inflammations and autoimmune diseases.

In another aspect the invention relates to a pharmaceutical preparation comprising a compound of general formula (1) or (1A) and at least one other cytostatic or cytotoxic active substance, different from formula (1) or (1A), optionally in the form of the tautomers, the racemates, the enantiomers, the diastereomers and the mixtures thereof, and optionally the pharmaceutically active salts thereof.

DEFINITIONS

As used herein, the following definitions apply, unless stated otherwise:

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl contains at least one triple bond. If a hydrocarbon chain were to carry both at least one double bond and also at least one triple bond, by definition it would belong to the alkynyl sub-group. All the sub-groups mentioned above may further be divided into straight-chain (unbranched) and branched. If an alkyl is substituted, the substitution may be mono- or polysubstitution in each case, at all the hydrogen-carrying carbon atoms, independently of one another.

Examples of representatives of individual sub-groups are listed below.

Straight-Chain (Unbranched) or Branched Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tert.-butyl (1,1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chain (Unbranched) or Branched Alkenyl:

vinyl (ethenyl); prop-1-enyl; allyl (prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. without any further definition are meant saturated hydrocarbon groups with the corresponding number of carbon atoms, all the isomeric forms being included.

By the terms propenyl, butenyl, pentenyl, hexenyl, heptenyl, octenyl, nonenyl, decenyl etc. without any further definition are meant unsaturated hydrocarbon groups with the corresponding number of carbon atoms and a double bond, all the isomeric forms, i.e. (Z)/(E) isomers, being included where applicable.

By the terms butadienyl, pentadienyl, hexadienyl, heptadienyl, octadienyl, nonadienyl, decadienyl etc. without any further definition are meant unsaturated hydrocarbon groups with the corresponding number of carbon atoms and two double bonds, all the isomeric forms, i.e. (Z)/(E) isomers, being included where applicable.

By the terms propynyl, butynyl, pentynyl, hexynyl, heptynyl, octynyl, nonynyl, decynyl etc. without any further definition are meant unsaturated hydrocarbon groups with the corresponding number of carbon atoms and a triple bond, all the isomeric forms being included.

By the term heteroalkyl are meant groups which can be derived from the alkyl as defined above in its broadest sense if, in the hydrocarbon chains, one or more of the groups —$CH_3$ are replaced independently of one another by the groups —OH, —SH or —$NH_2$, one or more of the groups —$CH_2$— are replaced independently of one another by the groups —O—, —S— or —NH—, one or more of the groups

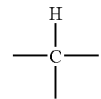

are replaced by the group

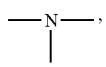

one or more of the groups =CH— are replaced by the group =N—, one or more of the groups =CH$_2$ are replaced by the group =NH or one or more of the groups CH are replaced by the group ≡N, while overall there may only be a maximum of three heteroatoms in a heteroalkyl, there must be at least one carbon atom between two oxygen atoms and between two sulphur atoms or between one oxygen and one sulphur atom and the group as a whole must be chemically stable.

It is immediately apparent from the indirect definition/derivation from alkyl that heteroalkyl is made up of the sub-groups saturated hydrocarbon chains with heteroatom(s), heteroalkenyl and heteroalkynyl, and one further subdivision may be carried out into straight-chain (unbranched) and branched. If a heteroalkyl is substituted, the substitution may be mono- or polysubstitution in each case, at all the hydrogen-carrying oxygen, sulphur, nitrogen and/or carbon atoms, independently of one another. Heteroalkyl itself may be linked to the molecule as a substituent both via a carbon atom and via a heteroatom.

Typical examples are listed below:
dimethylaminomethyl; dimethylaminoethyl (1-dimethylaminoethyl; 2-dimethylaminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylaminopropyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

Halogen denotes fluorine, chlorine, bromine and/or iodine atoms.

Haloalkyl is derived from alkyl as hereinbefore defined in its broadest sense, when one or more hydrogen atoms of the hydrocarbon chain are replaced independently of one another by halogen atoms, which may be identical or different. It is immediately apparent from the indirect definition/derivation from alkyl that haloalkyl is made up of the sub-groups saturated halohydrocarbon chains, haloalkenyl and haloalkynyl, and further subdivision may be made into straight-chain (unbranched) and branched. If a haloalkyl is substituted, the substitution may be mono- or polysubstitution in each case, at all the hydrogen-carrying carbon atoms, independently of one another.

Typical examples include —CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF=CF$_2$; —CCl=CH$_2$; —CBr=CH$_2$; —CI=CH$_2$; —C≡C—CF$_3$; —CHFCH$_2$CH$_3$; and —CHFCH$_2$CF$_3$.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). The term unsaturated means that in the ring system in question there is at least one double bond, but no aromatic system is formed. In bicyclic hydrocarbon rings two rings are linked such that they have at least two carbon atoms in common. In spirohydrocarbon rings one carbon atom (spiroatom) is shared by two rings. If a cycloalkyl is substituted, the substitution may be mono- or polysubstitution in each case, at all the hydrogen-carrying carbon atoms, independently of one another. Cycloalkyl itself may be linked to the molecule as substituent via any suitable position of the ring system.

Typical examples of individual sub-groups are listed below.
Monocyclic Saturated Hydrocarbon Rings:
cyclopropyl; cyclobutyl; cyclopentyl; cyclohexyl; cycloheptyl etc.
Monocyclic Unsaturated Hydrocarbon Rings:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.
Saturated and Unsaturated Bicyclic Hydrocarbon Rings:
bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl(decahydronaphthalene); bicyclo[2,2,1]heptyl(norbornyl); (bicyclo[2.2.1]hepta-2,5-dienyl(norborna-2,5-dienyl); bicyclo[2,2,1]hept-2-enyl (norbornenyl); bicyclo[4.1.0]heptyl(norcaranyl); bicyclo-[3.1.1]heptyl(pinanyl) etc.
Saturated and Unsaturated Spirohydrocarbon Rings:
spiro[2.5]octyl, spiro[3.3]heptyl, spiro[4.5]dec-2-ene etc.

Cycloalkylalkyl denotes the combination of the above-defined groups alkyl and cycloalkyl, in each case in their broadest sense. The alkyl group as substituent is directly linked to the molecule and is in turn substituted by a cycloalkyl group. The alkyl and cycloalkyl may be linked in both groups via any carbon atoms suitable for this purpose. The respective sub-groups of alkyl and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system. Typical examples include phenyl, naphthyl, indanyl (2,3-dihydroindenyl), 1,2,3,4-tetrahydronaphthyl and fluorenyl.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples include benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below.

Monocyclic Heteroaryls:

furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls:

indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydrothienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-5-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —$CH_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —$SO_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-5-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydro-pyrimidinyl; dihydrofuryl; dihydropyranyl; tetrahydrothienyl-5-oxide; tetrahydrothienyl-S,S-dioxide; homothiomorpholinyl-5-oxide; 2,3-dihydroazet; 2H-pyrrolyl; 4H-pyranyl; 1,4-dihydropyridinyl etc.

Bicyclic Heterorings (Saturated and Unsaturated):

8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl; hexahydro-furo[3,2-b]furyl; etc.

Spiro-Heterorings (Saturated and Unsaturated):

1,4-dioxa-spiro[4.5]decyl; 1-oxa-3,8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

By the term "suitable substituent" is meant a substituent that on the one hand is fitting on account of its valency and on the other hand leads to a system with chemical stability.

Preparation of the Compounds According to the Invention:

The compounds according to the invention may be prepared by the methods of synthesis described below, in which the substituents of general formulae (I to XIV) have the meanings given hereinbefore.

Method

Step 1

The intermediate compound III is prepared by substituting a leaving group LG, for example halogen, SCN or methoxy, preferably chlorine, at a heteroaromatic system I, by a nucleophile II.

Scheme 1

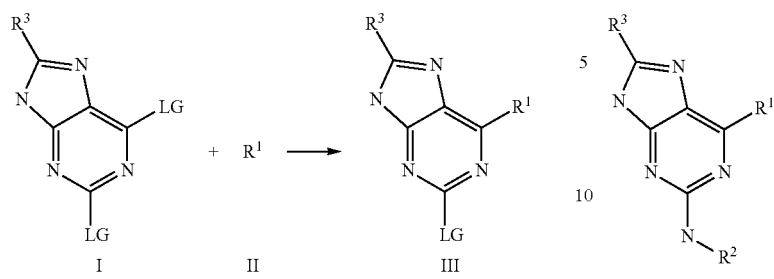

1 equivalent of compound I and 1 to 1.5 equivalents of compound II are stirred in a solvent, for example 1,4-dioxane, tetrahydrofuran, N,N-dimethyl-formamide, N,N-dimethylacetamide, 2-propanol, 2-butanol or water. After the addition of 2 to 2.5 equivalents of a base, for example potassium carbonate, sodium carbonate, caesium carbonate, N-ethyl-N,N-diisopropylamine or triethylamine, the reaction mixture is stirred for a further 1-72 h at a temperature of 25-50° C. Then the product is separated from an aqueous solution as a solid or the solvent is distilled off and the residue is purified by chromatography.

Step 2

The end compound V is prepared by substituting a leaving group LG, for example halogen, SCN or methoxy, preferably chlorine, at a heteroaromatic system III, by a nucleophile IV.

Scheme 2

1 equivalent of compound III and 1-3 equivalents of compound IV are stirred in a solvent, for example methanol, 1,4-dioxane, N,N-dimethylformamide, N,N-dimethylacetamide, N-methyl-2-pyrrolidinone, water or 1,1,1,6,6,6-hexafluoroisopropanol. At a temperature of 15-40° C., 1-5 equivalents of an inorganic acid, for example sulphuric acid or hydrochloric acid, are added. The reaction mixture is stirred for a further 0.5-16 h at a temperature of 95-160° C. Then the solvent is distilled off and the residue is purified by chromatography.

Step 3A

For the groups $R^2$, which may contain, in addition to the N atom already mentioned, a further N atom, a carbonyl group, a halogen atom or a further functional group, there is the possibility of further derivatisation to form secondary products.

For example, it is possible for molecules (VI) that have another N atom to be reacted with a reactant (VII) which contains a carbonyl group, to obtain products of type VIII:

Scheme 3A 1 equivalent of compound VI and 1-2 equivalents of compound VII are stirred in a solvent, for example MeOH or N,N-dimethylacetamide. At a temperature of 15-25° C., 2 to 5 equivalents of a reducing agent, for example sodium triacetoxyborohydride or sodium cyanoborohydride, are added. The reaction mixture is stirred for a further 0.5-18 h at a temperature of 15-25° C.

The reaction mixture is combined with water which has been adjusted to a pH of 8-9 with an inorganic base, for example sodium hydrogen carbonate, potassium carbonate or sodium hydroxide. This mixture is extracted 2-3 times with an organic solvent, for example diethyl ether, ethyl acetate or dichloromethane. The combined organic extracts are dried and the solvent is distilled off. Alternatively, after the reaction has ended, the solvent may be eliminated directly. The residue obtained is purified by chromatography or repeated crystallisation.

Step 3B

Molecules with another N atom in the group $R^2$ may be reacted with an alkane or haloalkane or an aryl or heteroaryl group with a leaving group (such as halide, mesylate, tosylate, etc), preferably halide.

Scheme 3B 1 equivalent of compound VI and 1-10 equivalents of compound IX are stirred in a solvent, for example 1,4-dioxane, tetrahydrofuran, N,N-dimethylformamide, acetonitrile or 1-methyl-2-pyrrolidone. At a temperature of 15-25° C., 2-2.5 equivalents of a base, for example potassium carbonate, sodium carbonate, caesium carbonate, N-ethyl-N,N-diisopropylamine or triethylamine, are added. The reaction mixture is stirred for a further 12-72 h at a temperature of 15-150° C. The reaction mixture is combined with water which has been adjusted to a pH of 8-9 with an inorganic base, for example sodium hydrogen carbonate or potassium carbonate. This mixture is extracted two to three times with an organic solvent, for example diethyl ether, ethyl acetate or dichloromethane. The combined organic extracts are dried and the solvent is distilled off. The residue is purified by chromatography or repeated crystallisation.

Chromatography

For the medium pressure chromatography (MPLC, normal phase) silica gel is used which is made by Millipore (named: Granula Silica Si-60A 35-70 µm) or C-18 RP-silica gel made by Macherey Nagel (named: Polygoprep 100-50 C18).

For the high pressure chromatography columns made by Waters (named: XTerra Prep. MS C18, 5 µM, 30×100 mm, Symmetric C18, 5 µm, 19×100 mm or XBridge C18, 5 µm, 19×100, Sunfire) are used.

Mass Spectroscopy/UV Spectrometer:

These data are obtained using a HPLC-MS apparatus (high performance liquid chromatography with mass detector) made by Agilent.

The apparatus is designed so that following on from the chromatography (column: Zorbax SB-C8, 3.5 µm, 2.1*50, Messrs. Agilent) a diode array detector (G1315B made by Agilent) and a mass detector (1100 LS-MSD SL; G1946D; Messrs. Agilent) are connected in series.

The apparatus is operated with a flow rate of 0.6 mL/min. For a separation process the liquid runs through a gradient within 3.5 min (start of gradient: 95% water and 5% acetonitrile; end of gradient: 5% water and 95% acetonitrile; 0.1% formic acid or 0.1% $NH_3/KHCO_3$ is added to each of the solvents as a buffer).

Starting Materials

Unless their preparation is described, the starting materials are commercially obtainable, known from the literature or readily accessible to the skilled man by methods in general use.

4,5,6,7-tetrahydro-1H-imidazo[4,5-c]pyridine (T. Vitali et al., Farmacao, Ed. Sci. 20, 636 (1969))

1-methyl-4,5,6,7-tetrahydro-1H-imidazo[4,5-c]pyridine (R. Jain, L. A. Cohen, Tetrahedron, 52 (15) 5363 (1996) or T. Vitali et al., Farmacao, Ed. Sci. 20, 636 (1969))

2-methyl-4,5,6,7-tetrahydro-1H-imidazo[4,5-c]pyridine and analogues (Y. M. Yutilov, N. N. Smolyar, N. V. Astashkina, Russ. J. Org. Chem. 38, 419.

3-methyl-4,5,6,7-tetrahydro-1H-imidazo[4,5-c]pyridine (G. Durant et al., J. Med. Chem. (1976), 19, 923 or T. Vitali et al., Farmacao, Ed. Sci. 20, 636 (1969))

4,5,6,7-tetrahydro-1H-imidazo[4,5-d]-azepine (WO03/032997)

2-methyl-4,5,6,7-tetrahydro-1H-imidazo[4,5-d]-azepine and derivatives (analogously to WO03/032997)

2-chloro-8-methyl-6-(1,4,6,7-tetrahydro-imidazo[4,5-c]pyridin-5-yl)-9H-purine or 2-chloro-8-ethyl-6-(1,4,6,7-tetrahydro-imidazo[4,5-c]pyridin-5-yl)-9H-purine (analogously to WO 05097135 with 4,5,6,7-tetrahydro-1H-imidazo[4,5-c]pyridine)

4-morpholin-4-yl-cyclohexylamine and 4-morpholin-4-yl-cyclobutylamine (WO2006/021544)

Aminobenzylamines are commercially obtainable or may be prepared analogously to Monatsh. Chem. (1969), 100(4) or by corresponding methods known to the skilled man.

4-Aminoanilines are commercially obtainable or may be prepared analogously to WO2006/021548 or by corresponding methods known to the skilled man.

1-methyl-1,4,5,6,7,8-hexahydro-imidazo[4,5-d]azepine

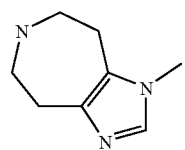

500 mg 6-benzyl-1,4,5,6,7,8-hexahydro-imidazo[4,5-d]azepin (WO 03/032997) are dissolved in 5 mL DMSO and combined with 271.5 mg potassium-tert.-butoxide. After 20 min 152 µL methyl iodide are added dropwise. After another 80 min the mixture is combined with saturated sodium hydrogen carbonate solution and extracted three times with dichloromethane. The combined organic phases are dried and freed from the solvent in vacuo. The residue is purified by column chromatography. The carrier material used is silica gel and a solvent mixture of 92% dichloromethane and 8% MeOH/aqueous $NH_3$ (9:1) is used. The suitable fractions are freed from the solvent in vacuo. The residue is dissolved in 25 mL concentrated acetic acid and combined with Pd/C. The mixture is hydrogenated for 5 h at 5 bar hydrogen pressure at 25° C. and then for 18 h at 60° C. Then the catalyst is filtered off, the solvent is eliminated in vacuo and the residue is again dissolved in 25 mL concentrated acetic acid and combined with Pd/C. The mixture is hydrogenated for 6 days at 60° C. Then the catalyst is filtered off and the solvent is eliminated in vacuo.

1-ethyl-1,4,5,6,7,8-hexahydro-imidazo[4,5-d]azepine is prepared analogously to 1-methyl-1,4,5,6,7,8-hexahydro-imidazo[4,5-d]azepine.

Example 1

(3,5-difluoro-4-morpholin-4-yl-phenyl)-[6-(3,4,6,7-tetrahydro-imidazol-[4,5-c]pyridin-5-yl)-9H-purin-2-yl]-amine

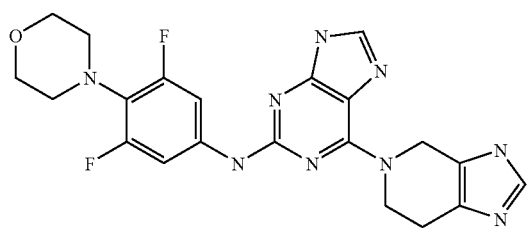 [SMILES: Fc1cc(Nc2nc(N3CCc4nc[nH]c4C3)c3nc[nH]c3n2)cc(F)c1N1CCOCC1]

a) 2-chloro-6-(3,4,6,7-tetrahydro-imidazol-[4,5-c]pyridin-5-yl)-9H-purine 1.36 g 2,6-dichloropurine are suspended in 10 mL of tetrahydrofuran and combined with 4.75 mL N,N-diisopropylethylamine and 1.51 g 4,5,6,7-tetrahydro-3H-imidazol-[4,5-c]pyridine. The reaction mixture is stirred for 14 h at 40° C. Then the solvent is eliminated in vacuo and the crude product is dissolved in N,N-dimethylformamide. After the addition of methanol a precipitate is formed, which is filtered off. After partial elimination of the solvent another precipitate is formed, which is filtered off.

Yield: 1.55 g
MS (ESI): 277 (M+H)$^+$ b) 4-(2,6-difluoro-4-nitro-phenyl)-morpholine 5.10 mL morpholine are dissolved in 1 mL 1-methyl-2-pyrrolidon and combined with 14.99 mL N,N-diisopropyl-ethylamine and 1.85 mL 3,4,5-trifluoronitrobenzene. The reaction mixture is stirred for 1 h at 110° C. After cooling the reaction mixture is diluted with 70 mL water and 15 mL concentrated aqueous HCl solution are added. The precipitate formed is filtered off, with water washed and dissolved with ethyl acetate. Then the solvent is eliminated in vacuo.

Yield: 3.88 g
MS (ESI): 245 (M+H)$^+$ c) 3,5-difluoro-4-morpholin-4-yl-phenylamine 3.88 g of 4-(2,6-difluoro-4-nitro-phenyl)-morpholine are dissolved in 50 mL methanol and combined with Pd/C. The mixture is hydrogenated for 18 h at 7 bar hydrogen pressure. Then the catalyst is filtered off and the solvent is eliminated in vacuo.

Yield: 3.36 g
to MS (ESI): 215 (M+H)$^+$ d) (3,5-difluoro-4-morpholin-4-yl-phenyl)-[6-(3,4,6,7-tetrahydro-imidazol-[4,5-c]pyridin-5-yl)-9H-purin-2-yl]-amine 0.13 g of 2-chloro-6-(3,4,6,7-tetrahydro-imidazol-[4,5-c]pyridin-5-yl)-9H-purine are dissolved in 0.40 mL 1,1,1,3,3,3-hexafluoro-2-propanol and combined with 0.05 g 3,5-difluoro-4-morpholin-4-yl-phenylamine. After the addition of 0.12 mL dioxanic HCl solution (4 N) the mixture is heated to 120° C. and stirred for 2 h at this temperature. After the solvent has been eliminated in vacuo the residue is purified by column chromatography. The carrier material used is C18-RP silica gel and the product is passed through a gradient that consists of 85% water and 15% acetonitrile at the starting point and 40% water and 60% acetonitrile at the finishing point. 0.1% NH$_3$KHCO$_3$ is added to each eluant. The suitable fractions are freeze-dried.

Yield: 18.7 mg
UV max: 282 nM
MS (ESI): 454 (M+H)$^+$

Examples 2-79

The following compounds are prepared by an analogous method to that described in Example 1.

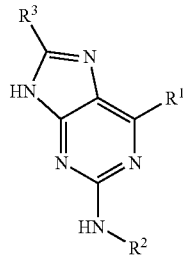

| No | R$^1$ | R$^2$ | R$^3$ | UVmax | Mass |
|---|---|---|---|---|---|
| 2 | X-[tetrahydroimidazopyridinyl] | X-[fluorophenoxy-tetrahydrofuranyl] | H | 266 | 437 |
| 3 | X-[tetrahydroimidazopyridinyl] | X-[fluorophenoxy-tetrahydrofuranyl] | H | 267 | 437 |

-continued
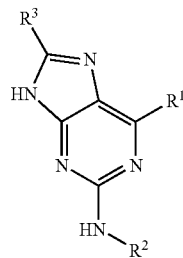
| No | R¹ | R² | R³ | UVmax | Mass |
|----|----|----|----|-------|------|
| 4 | X-N(imidazo-tetrahydropyridine) | X-phenyl(F)-O-tetrahydropyran-4-yl | H | 267 | 451 |
| 5 | X-N(imidazo-tetrahydropyridine) | X-phenyl(F)-N-(1-ethylpiperidin-4-yl) | H | 267 | 477 |
| 6 | X-N(imidazo-tetrahydropyridine) | X-phenyl(F)-N-(1-methylpiperidin-4-yl) | H | 269 | 463 |
| 7 | X-N(imidazo-tetrahydropyridine) | X-phenyl(F)-N-(tetrahydropyran-4-yl) | H | 276 | 450 |

-continued
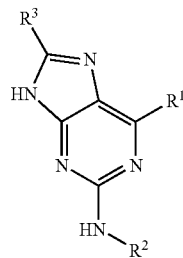
| No | R¹ | R² | R³ | UVmax | Mass |
|---|---|---|---|---|---|
| 8 | X-N(4,5,6,7-tetrahydroimidazo[4,5-c]pyridine) | X-phenyl-morpholine | H | 278 | 418 |
| 9 | X-N(4,5,6,7-tetrahydroimidazo[4,5-c]pyridine) | X-phenoxy-isosorbide | H | 266 | 477 |
| 10 | X-N(tetrahydroimidazo-azepine) | X-(2,6-difluoro-4-(1-ethylpiperidin-4-ylamino)phenyl) | H | 282 | 509 |
| 11 | X-N(tetrahydroimidazo-azepine) | X-phenyl-morpholine | H | 278 | 432 |

-continued
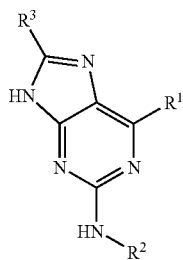
| No | R¹ | R² | R³ | UVmax | Mass |
|---|---|---|---|---|---|
| 12 | X-N(tetrahydroimidazopyridine) | X-(4-fluoro-phenyl)-N(methyl)-(1-ethylpiperidin-4-yl) | H | 270 | 477 |
| 13 | X-N(tetrahydroimidazopyridine) | X-phenyl-(2,6-difluoromorpholin-4-yl) | H | 282 | 454 |
| 14 | X-N(tetrahydroimidazopyridine) | X-(2-fluorophenyl)-NH-(1-cyclopropylpiperidin-4-yl) | H | 274 | 489 |
| 15 | X-N(tetrahydroimidazopyridine) | X-(3,5-difluorophenyl)-N(methyl) | H | 282 | 398 |

-continued
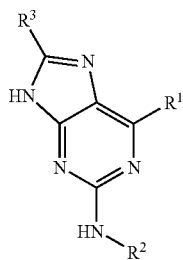
| No | R¹ | R² | R³ | UVmax | Mass |
|---|---|---|---|---|---|
| 16 | X-N(tetrahydroimidazopyridine) | 2-methyl-4-X-phenyl-N-(1-methylpiperidin-4-yl) | H | 274 | 459 |
| 17 | X-N(tetrahydroimidazopyridine) | 2-methoxy-4-X-phenyl-N-(1-methylpiperidin-4-yl) | H | 274 | 475 |
| 18 | X-N(tetrahydroimidazopyridine) | 2-bromo-4-X-phenyl-N-(1-cyclopropylpiperidin-4-yl) | H | 283 | 549/551 |
| 19 | X-N(tetrahydroimidazopyridine) | 2-chloro-4-X-phenyl-N-(1-methylpiperidin-4-yl) | H | 250 | 479 |

-continued
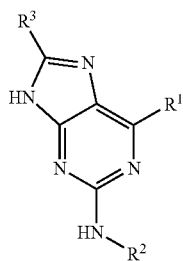
| No | R¹ | R² | R³ | UVmax | Mass |
|---|---|---|---|---|---|
| 20 | imidazo-azepine (X-N) | 4-(1-ethylpiperidin-4-ylamino)-2-fluorophenyl (X) | H | 278 | 491 |
| 21 | imidazo-azepine (X-N) | 4-(1-methylpiperidin-4-ylamino)-2-fluorophenyl (X) | H | 278 | 477 |
| 22 | imidazo-azepine (X-N) | 4-(1-cyclopropylpiperidin-4-ylamino)-2-fluorophenyl (X) | H | 276 | 503 |
| 23 | imidazo-azepine (X-N) | 4-(1-methylpiperidin-4-ylamino)-2-chlorophenyl (X) | H | 285 | 493 |

-continued
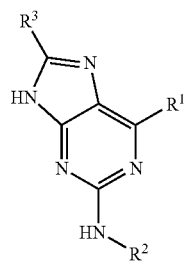
| No | R¹ | R² | R³ | UVmax | Mass |
|---|---|---|---|---|---|
| 24 | X—N(imidazo-azepine) | 4-X-2-Cl-phenyl-N(Me)-(1-methylpiperidin-4-yl) | H | 286 | 507 |
| 25 | X—N(imidazo-azepine) | 4-X-2-Cl-6-F-phenyl-N-(1-methylpiperidin-4-yl) | H | 286 | 511 |
| 26 | X—N(imidazo-azepine) | 4-X-2-Cl-phenyl-N-(1-cyclopropylpiperidin-4-yl) | H | 270 | 519 |
| 27 | X—N(imidazo-azepine) | 4-X-2-F-phenyl-morpholine | H | 280 | 450 |

-continued
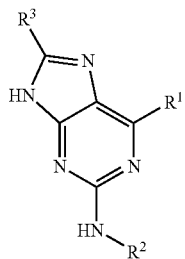
| No | R¹ | R² | R³ | UVmax | Mass |
|---|---|---|---|---|---|
| 28 | (X-N imidazo-azepine) | 4-X-2-Cl-phenyl-N(1-ethylpiperidin-4-yl) | H | 285 | 507 |
| 29 | (X-N imidazo-azepine) | 4-X-2-F-phenyl-N(tetrahydropyran-4-yl) | H | 278 | 464 |
| 30 | (X-N imidazo-azepine) | 4-X-phenyl-(2,6-dimethylmorpholin-4-yl) | H | 280 | 460 |
| 31 | (X-N imidazo-azepine) | 4-X-2-F-phenyl-(2,6-dimethylmorpholin-4-yl) | H | 278 | 478 |

-continued
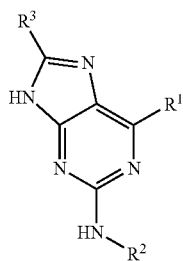
| No | R¹ | R² | R³ | UVmax | Mass |
|---|---|---|---|---|---|
| 32 | imidazo-azepine with X-N | 4-X, 2-Cl phenyl with 2,6-dimethylmorpholine | H | 486 | 494 |
| 33 | imidazo-azepine with X-N | 4-X, 2-Cl phenyl with tetrahydropyran-4-ylamino | H | 283 | 480 |
| 34 | imidazo-azepine with X-N | 4-X, 2-Cl phenyl with N-methyl-N-(tetrahydropyran-4-yl)amino | H | 288 | 494 |
| 35 | imidazo-azepine with X-N | 4-X, 3-Cl, 5-F phenyl with morpholine | H | 250 | 484 |

-continued
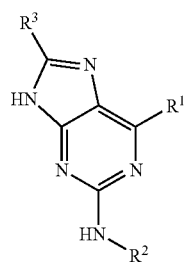
| No | R¹ | R² | R³ | UVmax | Mass |
|---|---|---|---|---|---|
| 36 | 5,6,7,8-tetrahydroimidazo-azepine with X-N | 4-X, 2-F, 6-Cl phenyl with N-(tetrahydropyran-4-yl) | H | 286 | 498 |
| 37 | 5,6,7,8-tetrahydroimidazo-azepine with X-N | 4-X, 2,6-diF phenyl with N-(1,2,2,6,6-pentamethylpiperidin-4-yl) | H | 274 | 551 |
| 38 | 4,5,6,7-tetrahydroimidazo-pyridine with X-N | 4-(morpholin-4-yl)phenyl-X | CH₃ | 284 | 432 |
| 39 | 4,5,6,7-tetrahydroimidazo-pyridine with X-N | 4-(4-methylpiperazin-1-yl)phenyl-X | CH₃ | 285 | 445 |

-continued
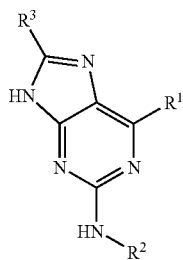
| No | R¹ | R² | R³ | UVmax | Mass |
|---|---|---|---|---|---|
| 40 | X-[4,5,6,7-tetrahydroimidazo[4,5-c]pyridin-5-yl] | X-[4-(morpholin-4-yl)phenyl] | $C_2H_5$ | 284 | 446 |
| 41 | X-[4,5,6,7-tetrahydroimidazo[4,5-c]pyridin-5-yl] | X-[4-(4-methylpiperazin-1-yl)phenyl] | $C_2H_5$ | 285 | 459 |
| 42 | X-[4,5,6,7,8-tetrahydroimidazo-azepin-6-yl] | X-[4-(morpholin-4-yl)phenyl] | H | 278 | 446 |
| 43 | X-[4,5,6,7-tetrahydroimidazo[4,5-c]pyridin-5-yl] | X-[2-fluoro-4-[(1-methylpiperidin-4-yl)amino]phenyl] | $C_2H_5$ | 280 | 491 |

-continued
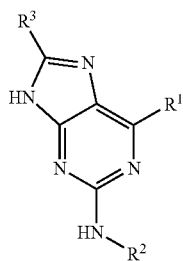
| No | R¹ | R² | R³ | UVmax | Mass |
|---|---|---|---|---|---|
| 44 | X-N(tetrahydroimidazopyridine) | 2-fluoro-4-X-phenyl-N-(1-methylpiperidin-4-yl) | CH₃ | 280 | 477 |
| 45 | X-N(methyl-tetrahydroimidazoazepine) | 2-fluoro-4-X-phenyl-N-(1-methylpiperidin-4-yl) | H | 278 | 491 |
| 46 | X-N(ethyl-tetrahydroimidazoazepine) | 4-X-phenyl-morpholine | H | 280 | 460 |
| 47 | X-N(ethyl-tetrahydroimidazoazepine) | 4-X-phenyl-morpholine | H | 270 | 505 |

-continued
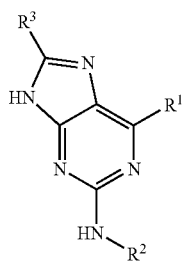
| No | R¹ | R² | R³ | UVmax | Mass |
|---|---|---|---|---|---|
| 48 | X-N tetrahydroimidazopyridine | 4-(morpholinomethyl)phenyl-X | H | 274 | 432 |
| 49 | X-N tetrahydroimidazopyridine | 4-((dimethylamino)methyl)phenyl-X | H | 266 | 390 |
| 50 | X-N tetrahydroimidazopyridine | 3-((dimethylamino)methyl)phenyl-X | H | 266 | 390 |
| 51 | X-N tetrahydroimidazopyridine | 3-(morpholinomethyl)phenyl-X | H | 266 | 432 |
| 52 | X-N tetrahydroimidazopyridine | 2-chloro-5-X-((dimethylamino)methyl)phenyl | H | 266 | 424 |

-continued
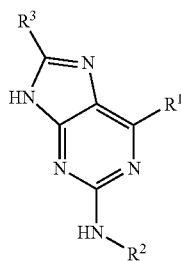
| No | R¹ | R² | R³ | UVmax | Mass |
|---|---|---|---|---|---|
| 53 | (X-N imidazo-azepine) | (X-phenyl-morpholine) | CH₃ | 285 | 446 |
| 54 | (X-N imidazo-pyridine) | (X-Cl-benzyl-morpholine) | H | 278 | 466 |
| 55 | (X-N imidazo-azepine) | (X-F-phenyl-N-methylpiperidine) | CH₃ | 273 | 491 |
| 56 | (X-N imidazo-azepine) | (X-Cl-benzyl-dimethylamine) | H | 274 | 438 |

-continued

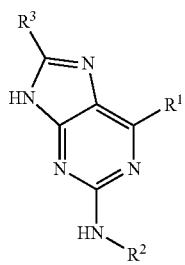

| No | R¹ | R² | R³ | UVmax | Mass |
|---|---|---|---|---|---|
| 57 | X-N(tetrahydroimidazo[4,5-c]pyridine, 2-methyl) | X-(4-morpholinophenyl) | H | 278 | 432 |
| 58 | X-N(tetrahydroimidazo[4,5-c]pyridine, 2-ethyl) | X-(4-morpholinophenyl) | H | 278 | 446 |
| 59 | X-N(tetrahydropyrazolo[4,3-c]pyridine) | X-(4-morpholinophenyl) | H | 278 | 418 |
| 60 | X-N(tetrahydroimidazo[4,5-c]pyridine) | X-(4-(dimethylamino)-2-((dimethylamino)methyl)phenyl) | H | 282 | 433 |
| 61 | X-N(tetrahydroimidazo[4,5-c]pyridine) | X-(2-((dimethylamino)methyl)-4-methoxyphenyl) | H | 266 | 420 |

-continued
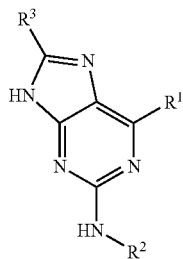
| No | R¹ | R² | R³ | UVmax | Mass |
|---|---|---|---|---|---|
| 62 | ![X-N piperidine fused imidazole, 3-methyl] | ![X-phenyl-morpholine] | H | 278 | 432 |
| 63 | ![X-N piperidine fused imidazole, 3-methyl] | ![X-phenyl-N-methylpiperazine] | H | 280 | 445 |
| 64 | ![X-N piperidine fused imidazole, 1-methyl] | ![X-phenyl-morpholine] | H | 278 | 432 |
| 65 | ![X-N piperidine fused imidazole, 1-methyl] | ![X-phenyl-N-methylpiperazine] | H | 280 | 445 |

-continued

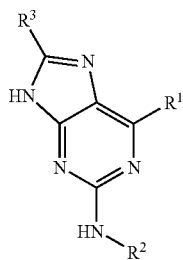

| No | R¹ | R² | R³ | UVmax | Mass |
|---|---|---|---|---|---|
| 66 | (X-N-containing fused imidazole-azepane, N-methyl) | 4-(morpholin-4-yl)phenyl-X | H | 278 | 446 |
| 67 | (X-N-containing fused imidazole-azepane, N-methyl) | 2-fluoro-4-X-phenyl with (1-methylpiperidin-4-yl)amino | H | 276 | 491 |
| 68 | (X-N-containing fused imidazole-azepane, N-ethyl) | 4-(morpholin-4-yl)phenyl-X | H | 280 | 460 |
| 69 | (X-N-containing fused imidazole-azepane, N-ethyl) | 2-fluoro-4-X-phenyl with (1-methylpiperidin-4-yl)amino | H | 278 | 505 |

-continued

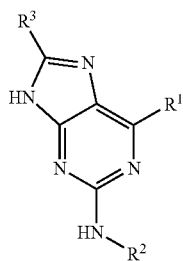

| No | R¹ | R² | R³ | UVmax | Mass |
|---|---|---|---|---|---|
| 70 | (7,8-dihydro-6H-imidazo[4,5-d]azepine with X on N, 2-(2-methoxyethyl) substituent) | 4-(morpholin-4-yl)phenyl, X at 4-position | H | 280 | 490 |
| 71 | (7,8-dihydro-6H-imidazo[4,5-d]azepine with X on N, 2-(2-methoxyethyl) substituent) | 2-fluoro-4-X-phenyl with (1-methylpiperidin-4-yl)amino at position 1 | H | 278 | 535 |
| 72 | (4,5,6,7-tetrahydro-1-methyl-imidazo[4,5-c]pyridine with X on N) | 2-fluoro-4-X-phenyl with (1-methylpiperidin-4-yl)amino at position 1 | H | 274 | 477 |
| 73 | (4,5,6,7-tetrahydro-3-(trifluoromethyl)-pyrazolo[4,3-c]pyridine with X on N) | 4-(morpholin-4-yl)phenyl, X at 4-position | H | 283 | 486 |

Example 74

[4-(1-cyclopropyl-piperidin-4-yl)-phenyl]-[6-(4,5,7,8-tetrahydro-1H-imidazo[4,5-d]azepin-6-yl)-9H-purin-2-yl]-amine

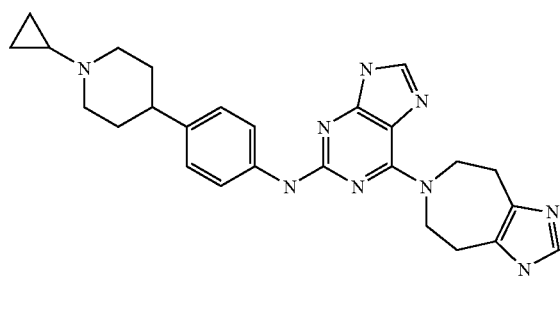 [SMILES: c1nc2c([nH]1)CCN(c1nc(Nc3ccc(C4CCN(C5CC5)CC4)cc3)nc3[nH]cnc13)CC2]

a) 1-cyclopropyl-4-(4-nitro-phenyl)-piperidine 0.50 g 4-(4-nitro-phenyl)-piperidine are dissolved in 1.5 mL methanol and combined with 0.80 g sodium cyanoborohydride and 2 µL glacial acetic acid. Then 0.97 mL [(1-ethoxycyclopropyl)oxy]trimethylsilane are added and the mixture is stirred for 24 h at 50° C. After cooling, 100 mL potassium hydrogen sulphate solution (10%) are added and the mixture is extracted twice with dichloromethane. The combined organic phases are dried, the solvent is eliminated in vacuo. The residue is used in the next stage of the synthesis without any further purification.

Yield: 0.57 g b) 4-(1-cyclopropyl-piperidin-4-yl)-phenyl amine 0.57 g 1-cyclopropyl-4-(4-nitro-phenyl)-piperidine are dissolved in 30 mL tetrahydrofuran and combined with Pd/C. The mixture is hydrogenated for 72 h at 7 bar hydrogen pressure. Then the catalyst is filtered off and the solvent is eliminated in vacuo. The residue is used in the next stage of the synthesis without any further purification.

Yield: 0.76 g c) [4-(1-cyclopropyl-piperidin-4-yl)-phenyl]-[6-(4,5,7,8-tetrahydro-1H-imidazo[4,5-d]azepin-6-yl)-9H-purin-2-yl]-amine 0.05 g 6-(2-chloro-9H-purin-6-yl)-1,4,5,6,7,8-hexahydro-imidazol-[4,5-d]azepin (prepared analogously to Example 1a) and 0.10 g 4-(1-cyclopropyl-piperidin-4-yl)-phenylamine are dissolved in 0.24 mL water and combined with 0.07 mL aqueous HCl (36%). This mixture is heated to 95° C. and stirred for 18 h at this temperature. After elimination of the solvent in vacuo the residue is purified by column chromatography. The carrier material used is C18-RP silica gel and the product is passed through a gradient that consists of 85% water and 15% acetonitrile at the starting point and 40% water and 60% acetonitrile at the finishing point. 0.1% NH₃KHCO₃ is added to both eluants. The suitable fractions are freeze-dried.

Yield: 4.00 mg
UV max: 270 nM
MS (ESI): 470 (M+H)⁺

Example 75

N-(1-ethyl-piperidin-4-yl)-N-methyl-N-[6-(1,4,6,7-tetrahydro-imidazol-[4,5-c]pyridin-5-yl)-9H-purin-2-yl]-benzene-1,4-diamine

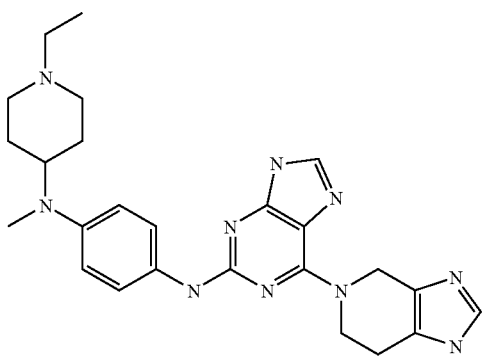 [SMILES: CCN1CCC(N(C)c2ccc(Nc3nc(N4CCc5[nH]cnc5C4)c4nc[nH]c4n3)cc2)CC1]

20 mg N-(1-ethyl-piperidin-4-yl)-N-[6-(1,4,6,7-tetrahydro-imidazol-[4,5-c]pyridin-5-yl)-9H-purin-2-yl]-benzene-1,4-diamine (cf Example 5) are dissolved in 0.3 mL N,N-dimethylacetamide. After the addition of 2 µL glacial acetic acid, 6.3 µL formaldehyde and 46.9 mg sodium triacetoxyborohydride the suspension is stirred for 2 h at RT. After the addition of 50 µL water the reaction solution is purified by column chromatography. The carrier material used is C18-RP silica gel and the product is passed through a gradient that consists of 85% water and 15% acetonitrile at the starting point and 5% water and 95% acetonitrile at the finishing point. 0.2% NH₃KHCO₃ is added to both eluants. The suitable fractions are freeze-dried.

Yield: 17 mg
UV max: 270 nM
MS (ESI): 491 (M+H)⁺

Example 76

N-(1-ethyl-piperidin-4-yl)-N-methyl-N-[6-(4,5,7,8-tetrahydro-1H-imidazol-[4,5-d]azepin-6-yl)-9H-purin-2-yl]-benzene-1,4-diamine

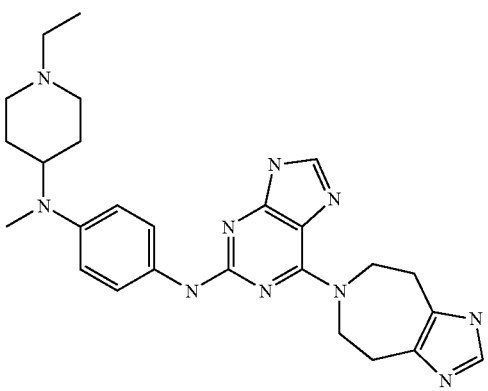 [SMILES: CCN1CCC(N(C)c2ccc(Nc3nc(N4CCc5nc[nH]c5CC4)c4nc[nH]c4n3)cc2)CC1]

The compound is prepared by an analogous method to that described in Example 75. The educt used here is N-(1-ethyl-piperidin-4-yl)-N-[6-(4,5,7,8-tetrahydro-1H-imidazol-[4,5-d]azepin-6-yl)-9H-purin-2-yl]-benzene-1,4-diamine (cf. Example 20).

UV max: 27 nM
MS (ESI): 505 (M+H)⁺

Example 77

2-fluoro-$N^4$-[6-(4,5,7,8-tetrahydro-1H-imidazo[4,5-d]azepin-6-yl)-9H-purin-2-yl]-$N^1$-[1-(2,2,2-trifluoroethyl)-piperidin-4-yl]-benzene-1,4-diamine

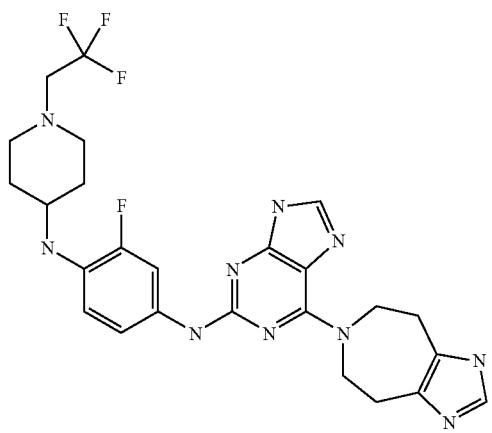 [SMILES: Fc1cc(Nc2nc(N3CCc4nc[nH]c4CC3)c3nc[nH]c3n2)ccc1NC1CCN(CC(F)(F)F)CC1]

40 mg of 2-fluoro-$N^1$-piperidin-4-yl-$N^4$-[6-(4,5,7,8-tetrahydro-1H-imidazo[4,5-d]azepin-6-yl)-9H-purin-2-yl]-benzene-1,4-diamine (prepared analogously to Example 1 from 2-chloro-6-(3,4,6,7-tetrahydroimidazo[4,5-c]pyridin-5-yl)-9H-purine and tert-butyl 4-(4-amino-2-fluoro-phenylamino)-piperidine-1-carboxylate), 12.86 μL of 2,2,2-trifluoroethyl-trifluoromethylsulphonate and 61.63 mg potassium carbonate are suspended in N,N-dimethylformamide and stirred for 2 h at 25° C. The reaction mixture is filtered to remove the insoluble constituents and the filtrate is purified by column chromatography. The carrier material used is C18-RP silica gel and the product is passed through a gradient that consists of 85% water and 15% acetonitrile at the starting point and 5% water and 95% acetonitrile at the finishing point. 0.2% $NH_3KHCO_3$ is added to both eluants. The suitable fractions are freeze-dried.

Yield: 15 mg

UV max: 250 nM

MS (ESI): 531 (M+H)$^+$

Example 78-83

The following compounds are prepared by an analogous method to that described in Example 77.

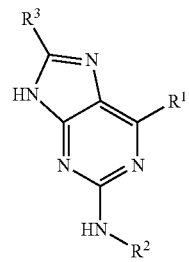

| No | R1 | R2 | R3 | UVmax | Mass |
|----|----|----|----|----|----|
| 78 | 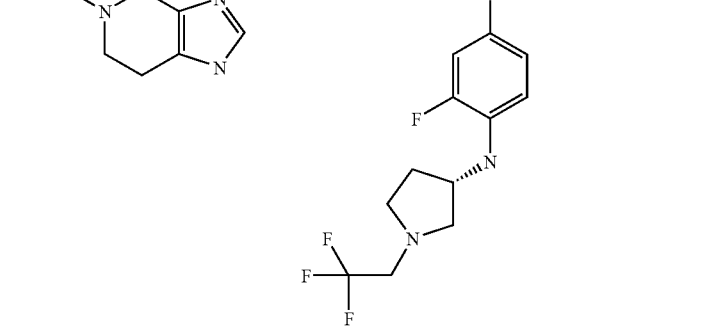 | | H | 250 | 517 |

-continued
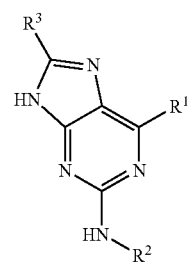
| No | R1 | R2 | R3 | UVmax | Mass |
|---|---|---|---|---|---|
| 79 | X-N(tetrahydroimidazopyridine) | 4-X-2-F-phenyl-N-[(3S)-1-(2,2,2-trifluoroethyl)pyrrolidin-3-yl] | H | 250 | 535 |
| 80 | X-N(tetrahydroimidazopyridine isomer) | 4-X-2,6-diF-phenyl-N-[1-(2,2,2-trifluoroethyl)pyrrolidin-3-yl] | H | 250 | 535 |
| 81 | X-N(tetrahydroimidazoazepine) | 4-X-2-F-phenyl-N-[1-(2,2-difluoroethyl)piperidin-4-yl] | H | 275 | 527 |
| 82 | X-N(tetrahydroimidazoazepine) | 4-X-2-F-phenyl-N-[1-(2-fluoroethyl)piperidin-4-yl] | H | 275 | 509 |

Example 83

2-fluoro-N⁴-[6-(4,5,7,8-tetrahydro-1H-imidazol-[4,5-d]azepin-6-yl)-9H-purin-2-yl]-N¹-(1-thiazol-2-yl-piperidin-4-yl)-benzene-1,4-diamine

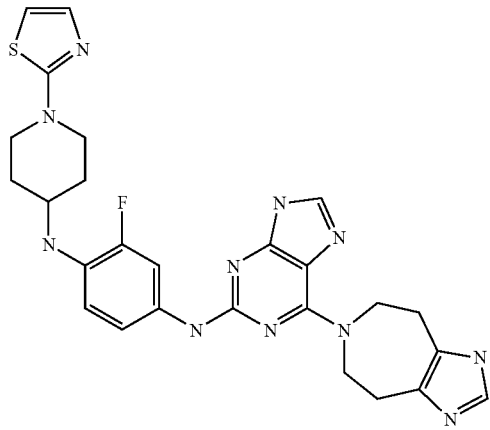 [SMILES: Fc1cc(Nc2nc(N3CCc4nc[nH]c4CC3)c3nc[nH]c3n2)ccc1NC1CCN(c2nccs2)CC1]

20 mg 2-fluoro-N¹-piperidin-4-yl-N⁴-[6-(4,5,7,8-tetrahydro-1H-imidazol-[4,5-d]azepin-6-yl)-9H-purin-2-yl]-benzene-1,4-diamine (prepared analogously to Example 1 from 6-(2-chloro-9H-purin-6-yl)-1,4,5,6,7,8-hexahydro-imidazol-[4,5-d]azepine and tert-butyl 4-(4-amino-2-fluoro-phenylamino)-piperidine-1-carboxylate), 14.63 mg 2-bromothiazole and 76 µL N,N-diisopropylethylamine are suspended in 100 µL 1-methyl-2-pyrrolidon and stirred for 30 min at 150° C. The reaction mixture is diluted with 20 mL dichloromethane and extracted twice with 25 mL water and saturated ammonium chloride solution. After elimination of the solvent in vacuo the residue is purified by column chromatography. The carrier material used is C18-RP-silica gel and the product is passed through a gradient that consists of 85% water and 15% acetonitrile at the starting point and 5% water and 95% acetonitrile at the finishing point. 0.2% $NH_3KHCO_3$ is added to both eluants. The suitable fractions are freeze-dried.

Yield: 6 mg
UV max: 275 nM
MS (ESI): 532 (M+H)⁺

Example 84

2-fluoro-N⁴-[6-(4,5,7,8-tetrahydro-1H-imidazol-[4,5-d]azepin-6-yl)-9H-purin-2-yl]-N¹—((R)-1-thiazol-2-yl-pyrrolidin-3-yl)-benzene-1,4-diamine

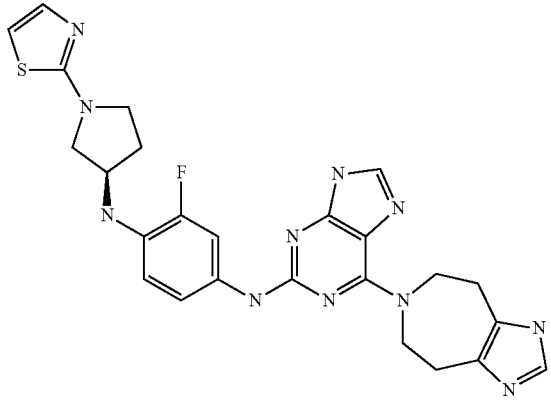 [SMILES: Fc1cc(Nc2nc(N3CCc4nc[nH]c4CC3)c3nc[nH]c3n2)ccc1N[C@@H]1CCN(c2nccs2)C1]

The compound is prepared by an analogous method to that described in Example 89. The educt used here is 2-fluoro-N¹—(R)-pyrrolidin-3-yl-N⁴-[6-(4,5,7,8-tetrahydro-1H-imidazo[4,5-d]azepin-6-yl)-9H-purin-2-yl]-benzene-1,4-diamine (prepared analogously to Example 1 from 6-(2-chloro-9H-purin-6-yl)-1,4,5,6,7,8-hexahydro-imidazol-[4,5-d]azepine and tert-butyl(R)-3-(4-amino-phenylamino)-pyrrolidine-1-carboxylate).

UV max: 290 nM
MS (ESI): 518 (M+H)⁺

Experimental Section (Biology)

The following Examples describe the biological activity of the compounds according to the invention without restricting the invention to these Examples.

The activity of the compounds according to the invention on various kinases, for example on serine-threonine kinase PDK1, is determined in in vitro kinase assays with recombinantly produced protein. The compounds exhibit a good to very good activity in this assay, i.e. for example an $IC_{50}$ value of less than 1 µmol/L, generally less than 0.1 µmol/L.

Example of PDK1 Kinase Assay

Recombinant human PDK1 Enzym (aa 52-556) linked at its N-terminal end to $His_6$ is isolated from baculovirus-infected insect cells. Purified enzyme may be obtained for example from the University of Dundee, Scotland. The following components are combined in a well of a 96-well round-based dish (Messrs. Greiner bio-one, No. 650101);

7.5 µL of compound to be tested in varying concentrations (e.g. starting at 10 µM, and diluted 1:5) in 3.33% DMSO (final concentration 1% DMSO)/assay buffer (50 mM Tris pH 7.5, 0.05% β-mercaptoethanol, 10 mM Mg-acetate)

7.5 µL PDK1 (10 ng/well) and PDKtide (KTFCGTPEYLAPEVRREPRILSEEEQEM-FRDFDYIADWC, synthesised by Pepceuticals Limited, Nottingham, United Kingdom; 25 µM final concentration) PDK1 and PDKtide are together diluted accordingly in assay buffer; PDKtide is present in this mixture as an 83.3 µM solution.

10 µL ATP solution (25 µM ATP with 0.5 µCi/well gamma-P33-ATP)

The reaction is started by adding the ATP solution and the mixture is incubated for 30 min at ambient temperature; at the start of the reaction the dishes are shaken gently. The reaction is stopped by the addition of 5 µL/well 0.5 M phosphoric acid ($H_3PO_4$) and incubated for about 20 min at ambient temperature. The precipitate is transferred by harvesting onto filter plates (96-well microtitre filter plate: UniFilter GF/C; Messrs Perkin Elmer; No. 6005174), then washed 6 times with 50 mM $H_3PO_4$ and dried at 60° C. Then the plate is stuck down with sealing tape, 25 µL/well of scintillation solution (Microscint™ 0; Messrs. Perkin Elmer; No. 6013611) are added and the amount of P33 precipitated is measured using the Wallac Betacounter. The measured data are evaluated using GraphpadPrism® software.

The antiproliferative activity of the compounds according to the invention is determined on cultivated human tumour cells, for example on PC-3 cells. The compounds exhibit good to very good activity, i.e. for example an $EC_{50}$ value in the PC-3 proliferation test of less than 5 µmol/L, generally less than 1 µmol/L.

Measurement of the Inhibition of Proliferation on Cultivated Human Tumour Cells

To measure proliferation on cultivated human tumour cells, cells of prostate carcinoma tumour cell line PC-3 (obtained from American Type Culture Collection (ATCC)) are cultivated in Ham's F12K (Gibco®) and 10% foetal calf serum (Gibco®) and harvested in the log growth phase. Then the PC-3 cells are placed in 96-well plates (Costar) at a density of 2000 cells per well and incubated overnight in an incubator (at 37° C. and 5% CO$_2$), while on each plate 16 wells are used as controls (8 wells with cells to which only DMSO solution has been added (should yield 30-50% maximum value of reduced alamarBlue®), 4 wells containing only medium (medium control, after the addition of oxidised alamarBlue® reagent the background signal is obtained) and 4 wells where again only medium is added (after the addition of reduced alamarBlue® reagent it acts as a maximum value)). The active substances are added to the cells in various concentrations (dissolved in DMSO; DMSO final concentration: 0.2%) (in each case as a double or triple measurement). After 5 days' incubation 20 µl alamarBlue® reagent (Serotec) are added to each well and the cells are incubated for a further 5-7 hours. As a control, 20 µl reduced alamarBlue® reagent is added to each of 4 wells (alamarBlue® reagent which is autoclaved for 30 min). After incubation the colour change of the alamarBlue® reagent in the individual wells is determined in a SpectraMax® Photometer (Molecular Devices) (extinction 530 nm, emission 590 nm, 5 sec measuring time). The amount of alamarBlue® reagent reacted represents the metabolic activity of the cells. The relative cell activity is calculated in relation to the control (PC-3 cells without inhibitor) and the active substance concentration which inhibits the cell activity by 50% (EC50) is derived. The values are calculated from the average of two or three individual measurements.

The compounds according to the invention are also tested accordingly on other tumour cells. For example, these compounds are active on carcinomas of all kinds of tissue, e.g. glioblastoms (U87), ovarian carcinoma (SKOV-3), prostate carcinoma (LNCaP), mammary carcinoma (MDA-MB468), colon carcinoma (HCT116), lung carcinoma (H460), but also sarcomas (e.g. MES-SA, SK-UT-1B), and could be used for such indications, particularly for indications that comprise activating changes in the PI3K-AKT-PDK1 signal pathway. This is evidence of the broad range of applications of the compounds according to the invention for the treatment of all kinds of tumours.

The substances of the present invention inhibit PDK1 kinase. In view of their biological properties the new compounds of general formula (1) or (1A), the isomers thereof and the physiologically acceptable salts thereof are suitable for the treatment of diseases characterised by excessive or abnormal cell proliferation.

For example, the following cancers may be treated with compounds according to the invention, without being restricted thereto:
brain tumours such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumour such as prolactinoma, hypophyseal incidentaloma, HGH (human growth hormone) producing adenoma and corticotrophic adenoma, craniopharyngiomas, medulloblastoma, meningeoma and oligodendroglioma; nerve tumours such as for example tumours of the vegetative nervous system such as neuroblastoma, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus and duodenum; eyelid tumours (basalioma or adenocarcinoma of the eyelid apparatus); retinoblastoma; carcinoma of the pancreas; carcinoma of the bladder; lung tumours (bronchial carcinoma—small-cell lung cancer (SCLC), non-small-cell lung cancer (NSCLC) such as for example spindle-cell plate epithelial carcinomas, adenocarcinomas (acinary, paillary, bronchiolo-alveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukaemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma—mucinous or serous cystoma, endometriodal tumours, clear cell tumour, Brenner's tumour); gall bladder cancer; bile duct cancer such as for example Klatskin tumour; testicular cancer (germinal or non-germinal germ cell tumours); laryngeal cancer such as for example supra-glottal, glottal and subglottal tumours of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumour, Ewing's sarcoma, and plasmocytoma, head and neck tumours (HNO tumours) such as for example tumours of the lips, and oral cavity (carcinoma of the lips, tongue, oral cavity), nasopharyngeal carcinoma (tumours of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumours of the paranasal sinuses and nasal cavity, tumours of the salivary glands and ears; liver cell carcinoma (hepatocellular carcinoma (HCC); leukaemias, such as for example acute leukaemias such as acute lymphatic/lymphoblastic leukaemia (ALL), acute myeloid leukaemia (AML); chronic lymphatic leukaemia (CLL), chronic myeloid leukaemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumour); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) or (1A) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, lapatinib and trastuzumab); signal transduction inhibitors (e.g. imatinib and sorafenib); antimetabolites (e.g. antifolates such as methotrexate, premetrexed and raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions, —particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above. For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples that follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |

| C) Ampoule solution | |
|---|---|
| active substance according to formula (1) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

SEQUENCE LISTING

```
<160> NUMBER OF SEQ ID NOS: 2

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Lys Thr Phe Cys Gly Thr Pro Glu Tyr Leu Ala Pro Glu Val Arg Arg
1               5                   10                  15

Glu Pro Arg Ile Leu Ser Glu Glu Glu Gln Glu Met Phe Arg Asp Phe
            20                  25                  30

Asp Tyr Ile Ala Asp Trp Cys
        35

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6X His Tag

<400> SEQUENCE: 2

His His His His His His
1               5
```

-continued

| B) Tablets | per tablet |
|---|---|
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

The invention claimed is:

1. A compound of formula (1),

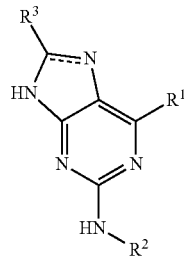

wherein
the dotted line represents an optional double bond and when there is no double bond, N is further substituted by hydrogen;

$R^1$ denotes tetrahydroimidazopyridine or tetrahydroimidazoazepine, optionally substituted by one or more identical or different $R^4$, and;

$R^2$ denotes a group selected from among $C_{6-15}$aryl, 3-8 membered heterocycloalkyl and 5-12 membered heteroaryl, optionally substituted by one or more identical or different $R^4$, and $R^3$ denotes hydrogen or a group selected from among =O, halogen and $C_{1-4}$alkyl; and $R^4$ denotes a group selected from among $R^a$, $R^b$ and $R^a$ substituted by one or more identical or different $R^c$ and/or $R^b$;

each $R^a$ is selected independently of one another from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —$CN$, —$NC$, —$OCN$, —$SCN$, —$NO$, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$ and —$N(R^g)C(NR^g)NR^cR^c$, each $R^c$ independently of one another denotes hydrogen or a group selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, each optionally substituted by one or more identical or different $R^d$ and/or $R^e$;

each $R^d$ is independently selected from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —$CN$, —$NC$, —$OCN$, —$SCN$, —$NO$, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$—$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$ and —$N(R^g)C(NR^g)NR^eR^e$, each $R^e$ independently of one another denotes hydrogen or a group selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, optionally substituted by one or more identical or different $R^f$ and/or $R^g$;

each $R^f$ is independently selected from among halogen and —$CF_3$; and each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, the compound optionally being in the form of the tautomers, the racemates, the enantiomers, the diastereomers and the mixtures thereof, and optionally the pharmacologically acceptable acid addition salts thereof.

2. A compound of formula (1A)

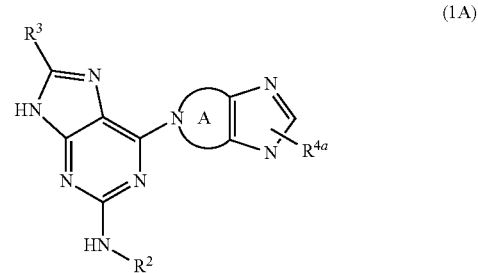

(1A)

wherein
A together with the N and the two fused carbon atoms denotes a 5-7 membered aliphatic ring wherein the other ring members are $CH_2$, $R^2$ denotes a group selected from among $C_{6-15}$aryl, 3-8 membered heterocycloalkyl and 5-12 membered heteroaryl, optionally substituted by one or more identical or different $R^4$, and $R^3$ denotes hydrogen or a group selected from among halogen and $C_{1-4}$alkyl; and $R^4$ and $R^{4a}$ in each case independently of one another denote a group selected from among $R^a$, $R^b$ and $R^a$ substituted by one or more identical or different $R^b$ and/or $R^c$;

each $R^a$ is selected independently of one another from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$ and —$N(R^g)C(NR^g)NR^cR^c$, each $R^c$ independently of one another denotes hydrogen or a group selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, optionally substituted by one or more identical or different $R^d$ and/or $R^e$;

each $R^d$ is independently selected from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —CN, —NC, —OCN, —SCN, —NO, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$—$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NRgNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$ and —$N(R^g)C(NR^g)NR^eR^e$, each $R^e$ independently of one another denotes hydrogen or a group selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, optionally substituted by one or more identical or different $R^f$ and/or $R^g$;

each $R^f$ is independently selected from among halogen and —$CF_3$; and each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl or 6-18 membered heteroarylalkyl, the compound optionally being in the form of the tautomers, the racemates, the enantiomers, the diastereomers and the mixtures thereof, and optionally the pharmacologically acceptable acid addition salts thereof.

3. A compound according to claim 2, wherein A together with the N and the two fused carbon atoms denotes a 6 or 7 membered ring wherein the other ring members are $CH_2$.

4. A compound according to claim 2, wherein $R^{4a}$ denotes a group selected from among hydrogen, halogen, —$CF_3$ and $C_{1-6}$alkyl, wherein the alkyl group is optionally substituted by —$R^e$.

5. A compound according to claim 1, wherein $R^2$ is a group selected from among $C_{6-10}$aryl and 5-12 membered heteroaryl, optionally substituted by one or more identical or different $R^4$.

6. A compound according to claim 5, wherein $R^2$ is phenyl, optionally substituted by one or more identical or different $R^4$.

7. A compound according to claim 1, wherein $R^3$ is a group selected from among hydrogen and $C_{1-6}$alkyl.

8. A pharmaceutical composition containing as active substance one or more compounds of formula (1) according to claim 1 or the pharmaceutically effective salts thereof, optionally in combination with conventional excipients and/or carriers.

9. A pharmaceutical composition comprising a compound of formula (1) according to claim 1 and at least one other cytostatic or cytotoxic active substance different from formula (1), optionally in the form of the tautomers, the racemates, the enantiomers, the diastereomers and the mixtures thereof, and optionally the pharmaceutically active salts thereof.

10. A pharmaceutical composition comprising a compound of formula (1A) according to claim 2 and at least one other cytostatic or cytotoxic active substance different from formula (1A), optionally in the form of the tautomers, the racemates, the enantiomers, the diastereomers and the mixtures thereof, and optionally the pharmaceutically active salts thereof.

11. A pharmaceutical composition containing as active substance one or more compounds of formula (1A) according to claim 2 and or the pharmaceutically effective salts thereof, optionally in combination with conventional excipients and or carriers.

* * * * *

UNITED STATES PATENT AND TRADEMARK OFFICE
CERTIFICATE OF CORRECTION

| | | |
|---|---|---|
| PATENT NO. | : 8,404,674 B2 | Page 1 of 1 |
| APPLICATION NO. | : 12/595072 | |
| DATED | : March 26, 2013 | |
| INVENTOR(S) | : Stadtmueller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 743 days.

Signed and Sealed this
Eleventh Day of February, 2014

Michelle K. Lee
*Deputy Director of the United States Patent and Trademark Office*